(12) United States Patent
Bissantz et al.

(10) Patent No.: US 7,790,752 B2
(45) Date of Patent: Sep. 7, 2010

(54) INDOL-3-YL-CARBONYL-AZASPIRO DERIVATIVES

(75) Inventors: Caterina Bissantz, Village-Neuf (FR); Christophe Grundschober, Rodersdorf (CH); Hasane Ratni, Habsheim (FR); Mark Rogers-Evans, Binningen (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 723 days.

(21) Appl. No.: 11/524,978

(22) Filed: Sep. 21, 2006

(65) Prior Publication Data

US 2007/0072888 A1    Mar. 29, 2007

(30) Foreign Application Priority Data

Sep. 28, 2005  (EP)  .................. 05108966

(51) Int. Cl.
*A61K 31/438* (2006.01)
*C07D 401/14* (2006.01)

(52) U.S. Cl. ............... 514/323; 546/184; 546/192; 546/196; 546/201; 514/315; 514/317; 514/320

(58) Field of Classification Search ............. 546/184, 546/192, 196, 201; 514/315, 317, 320, 323
See application file for complete search history.

(56) References Cited

U.S. PATENT DOCUMENTS

| | | | | |
|---|---|---|---|---|
| 7,332,501 B2 * | 2/2008 | Bissantz et al. | ............. | 514/278 |
| 7,351,706 B2 * | 4/2008 | Bissantz et al. | .......... | 514/230.5 |
| 7,432,259 B2 * | 10/2008 | Bissantz et al. | .......... | 514/230.5 |

FOREIGN PATENT DOCUMENTS

| WO | WO 98/28292 A1 | 7/1998 |
|---|---|---|
| WO | WO 2004/022558 A2 | 3/2004 |
| WO | WO 2004/104004 A2 | 12/2004 |

OTHER PUBLICATIONS

Database Chemcats Chemical Abstract Service, Columbus, Ohio, US retrieved from STN, XP002405277 & "Aurora Screening Library" (2006) Aurora Fine Chemicals, Graz, Austria.
Ebner, et al. (2002), Eur. J. Neurosci. vol. 15 pp. 384-388.
Liebsch et al. (1995), Regul. Pept. vol. 59 pp. 229-239.
Michelini et al., (1999), Annals NY Academy of Sciences vol. 897 pp. 198-211.
Van Kerckhoven et al., (2002), Eur. J. of Pharmacology vol. 449 pp. 135-141.
Swain, et al., J. Med. Chem. (1991), vol. 34, pp. 140-151.
Delgado et al., J. Org. Chem. (1993), vol. 58, pp. 2862-2866.
Bergman et al., J. Heterocyclic Chem. (1977), vol. 14, p. 1123-1134.

* cited by examiner

*Primary Examiner*—Golam M Shameem
(74) *Attorney, Agent, or Firm*—George W. Johnston; Patricia S. Rocha-Tramaloni; Kimberly J. Prior

(57) ABSTRACT

This invention relates to indol-3-yl-carbonyl-azaspiro derivatives which act as V1a receptor antagonists and which are represented by Formula I:

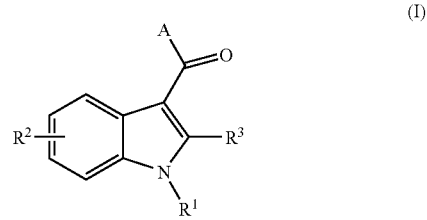

wherein the azaspiro-head group A and the residues $R^1$, $R^2$ and $R^3$ are as defined herein. The invention further relates to pharmaceutical compositions containing such compounds, their use for treating dysmenorrhea, hypertension, chronic heart failure, inappropriate secretion of vasopressin, liver cirrhosis, nephrotic syndrome, obsessive compulsive disorder, anxiety and depressive disorders, and methods of preparation thereof.

19 Claims, No Drawings

INDOL-3-YL-CARBONYL-AZASPIRO DERIVATIVES

PRIORITY TO RELATED APPLICATIONS

This application claims the benefit of European Application No. 05108966.2, filed Sep. 28, 2005, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-copping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann N Y Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

Thus vasopressin receptor antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders.

SUMMARY OF THE INVENTION

The present invention provides compounds of formula (I):

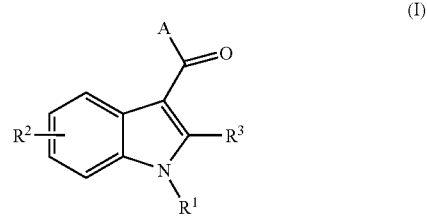

wherein $R^1$ is
  H,
  $C_{1-6}$-alkyl,
  aryl, 5 or 6 membered heteroaryl or sulfonylaryl, each of which is optionally substituted by one or more B,
  —$(CH_2)_m$—$R^a$ wherein $R^a$ is:
    CN,
    $OR^i$,
    $NR^iR^{ii}$, or
    $C_{3-6}$-cycloalkyl, 4 to 7 membered-heterocycloalkyl, aryl, or 5 or 6 membered heteroaryl, each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl, each of which is optionally substituted by one or more B, or $R^1$ and $R^3$ together with the indole ring to which they are attached form a 5 or 6 membered heterocycloalkyl which is optionally substituted by =O;

there is one or more $R^2$, wherein each $R^2$ is the same or different, $R^2$ is one or more H,
  OH,
  halo,
  CN,
  nitro,
  $C_{1-6}$-alkyl optionally substituted by —$NR^{iii}R^{iv}$,
  $C_{1-6}$-alkoxy,
  —O—$CH_2$—$C_{2-6}$-alkenyl, or
  benzyloxy, or two $R^2$ together with the indole ring to which they are attached-form an oxo or dioxo bridge;

$R^3$ is H,
  halo,
  —(CO)—$R^c$, wherein $R^c$ is:
    $C_{1-6}$-alkyl,
    —$(CH_2)_n$—$NR^iR^{ii}$,
    —$(CH_2)_n$—$NR^{iii}R^{iv}$,
    5 or 6 membered heterocycloalkyl optionally substituted by $C_{1-6}$-alkyl, or $C_{1-6}$-alkyl or aryl, each of which is optionally substituted by
halo,
—O(CO)—$C_{1-6}$-alkyl, or
—NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O) $NR^iR^{ii}$,
—C(O)—$C_{1-6}$-alkyl,
—S(O)$_2$—$C_{1-6}$-alkyl,
—S(O)$_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —S(O)$_2$—$C_{1-6}$-alkyl, and —S(O)$_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;

$R^{iii}$ and $R^{iv}$ are each independently H or $C_{1-6}$-alkyl;

m is 1 to 6;

n is 0 to 4; and

A is either a group of the formula (a) or (b):

(a)
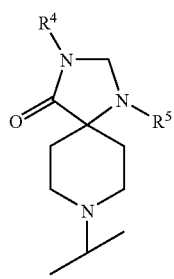

(b)
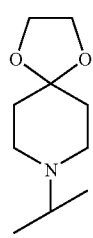

wherein
$R^4$ is is H or $C_{1-6}$-alkyl; and
$R^5$ is aryl optionally substituted by halo;
or a pharmaceutically acceptable salt thereof.

The compounds of formula (I) can contain some asymmetric carbon atoms. Accordingly, the present invention includes all stereoisomeric forms of the compounds of formula (I), including each of the individual enantiomers and mixtures thereof.

The invention also provides pharmaceutical compositions containing the compounds of the invention and a pharmaceutically acceptable carrier as well as processes for preparation of such compounds and compositions.

Compounds of formula (I) have good activity on the V1a receptor. Therefore, the invention provides methods for the treatment of dysmenorrhea, hypertension, chronic heart failure, inappropriate secretion of vasopressin, liver cirrhosis, nephrotic syndrome, obsessive compulsive disorder, anxiety and depressive disorders. Such methods comprise administering a therapeutically effective amount of a compound of formula (I) or a pharmaceutically acceptable salt thereof.

The preferred indications with regard to the present invention are the treatment of anxiety and depressive disorders.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety consisting of a mono-, bi- or tricyclic aromatic ring. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, and diphenylisopropylidenyl, as well as those specifically illustrated by the examples herein below. Substituents for aryl include, but are not limited to, halogen, $C_{1-6}$-alkyl, and $C_{1-6}$-alkoxy. Preferred aryl are phenyl and naphthyl, and still more preferably phenyl. The aryl moieties of the invention further can be ortho substituted by two substituents which together with the carbons of the aryl moiety form a fused, saturated or partially saturated, 5- to 6-membered ring containing one or two heteroatoms selected from O and N. Preferably the additional ring is a 5- to 6-membered ring containing two oxygen atoms. Examples of such substituted aryl moieties include, but are not limited to, benzodioxanyl, dihydro-benzofuranyl, benzodioxolyl, benzopyranyl, benzoxazinyl, benzoxazinonyl, benzopiperidinyl, benzopiperazinyl, benzopyrrolidinyl, benzomorpholinyl, methylenedioxyphenyl, ethylenedioxyphenyl, as well as those specifically illustrated by the examples herein below.

The term "$C_{1-6}$-alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl and the like. Preferred $C_{1-6}$-alkyl groups are $C_{1-4}$-groups, i.e. with 1-4 carbon atoms.

The term "$C_{1-6}$-alkoxy" denotes an alkyl group as defined above, attached via an oxygen atom. Preferred $C_{1-6}$-alkoxy groups are methoxy and ethoxy as well as those specifically illustrated by the examples herein below.

The term "$C_{2-6}$-alkenyl" denotes a carbon chain of 2 to 6 carbon atoms comprising at least one double bond in its chain. $C_{2-6}$-alkenyl groups include ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "benzyloxy" denotes a benzyl group attached via an oxygen atom.

The term "halogen" or "halo" denotes chlorine (Cl), iodine (I), fluorine (F) and bromine (Br).

The term "$C_{1-6}$-haloalkyl" denotes a $C_{1-6}$-alkyl group as defined above which is substituted by one or more halogen atom. Examples of $C_{1-6}$-haloalkyl include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-6}$-haloalkyl are difluoro- or trifluoro-methyl or ethyl.

"$C_{1-6}$-haloalkoxy" denotes a $C_{1-6}$-alkoxy group as defined above which is substituted by one or more halogen atom. Examples of $C_{1-6}$-haloalkoxy include, but are not limited to, methoxy or ethoxy, substituted by one or more Cl, F, Br or I atom(s) as well as those groups specifically illustrated by the examples herein below. Preferred $C_{1-6}$-haloalkoxy are difluoro- or trifluoro-methoxy or ethoxy.

The term "$C_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "4 to 7 membered heterocycloalkyl" means a monovalent saturated moiety, consisting of one ring having 4 to 7 atoms as ring members, containing one, two, or three heteroatoms chosen from nitrogen, oxygen or sulfur, the rest of the ring atoms being carbon atoms 4 to 7 membered heterocycloalkyl can optionally be substituted with one, two, three or four substituents, wherein each, substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heterocyclic moieties include, but are not limited to, optionally substituted oxetane, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein. Substituents can be selected from $C_{1-6}$-alkyl, $C_{1-6}$-alkoxy, $C_{1-6}$-halo alkyl, halo, CN, OH, $NH_2$, as well as those substituents which are specifically illustrated in the examples hereinafter.

The term "5 or 6 membered heteroaryl" means an aromatic ring having 5 or 6 ring atoms as ring members, containing one, two, or three ring heteroatoms selected from N, O, or S, the rest of the ring atoms being carbon atoms. 5 or 6 heteroaryl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "sulfonylaryl" denotes an aryl group as defined hereinabove which is attached via a sulfonyl group.

The expression "two $R^2$ together with the indole ring to which they are attached form an oxo or dioxo bridge" denotes an oxo or dioxo bridge of the following formulae:

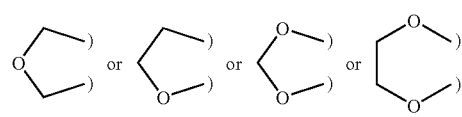

which bind two adjacent carbon atoms of the phenyl or indole ring of the compound of formula (I) to which either $R^2$ is binding.

Examples of groups illustrating the expression "$R^1$ and $R^3$ together with the indole ring to which they are attached form a 5 or 6 membered heterocycloalkyl which is optionally substituted by =O" are:

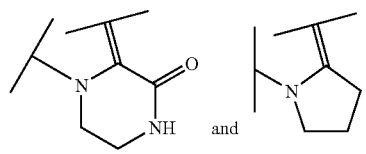

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid, as well as those specifically illustrated by the examples herein below.

"Therapeutically effective amount" means an amount that is effective to prevent, alleviate or ameliorate symptoms of disease or prolong the survival of the subject being treated.

The present invention provides compounds of formula (I):

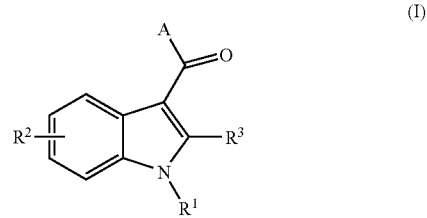

wherein

R¹ is
H,
C_{1-6}-alkyl,
aryl, 5 or 6 membered heteroaryl or sulfonylaryl, each of which is optionally substituted by one or more B,
—(CH_2)_m—R^a wherein R^a is:
CN,
OR^i,
NR^iR^{ii}, or
C_{3-6}-cycloalkyl, 4 to 7 membered-heterocycloalkyl, aryl, or 5 or 6 membered heteroaryl, each of which is optionally substituted by one or more B,
or —(CH_2)_n—(CO)—R^b or —(CH_2)_n—(SO_2)—R^b, wherein R^b is:
C_{1-6}-alkyl,
C_{1-6}-alkoxy,
C_{3-6}-cycloalkyl,
—(CH_2)_m—NR^{iii}R^{iv},
NR^iR^{ii}, or
C_{3-6}-cycloalkyl, 4 to 7 membered-heterocycloalkyl, aryl, or 5 or 6 membered heteroaryl, each of which is optionally substituted by one or more B,
or R¹ and R³ together with the indole ring to which they are attached form a 5 or 6 membered heterocycloalkyl which is optionally substituted by =O;

there is one or more R², wherein each R² is the same or different,

R² is one or more H,
OH,
halo,
CN,
nitro,
C_{1-6}-alkyl optionally substituted by —NR^{iii}R^{iv},
C_{1-6}-alkoxy,
—O—CH_2—C_{2-6}-alkenyl, or
benzyloxy, or two R² together with the indole ring to which they are attached form an oxo or dioxo bridge;

R³ is H,
halo,
—(CO)—R^c, wherein R^c is:
C_{1-6}-alkyl,
—(CH_2)_n—NR^iR^{ii},
—(CH_2)_n—NR^{iii}R^{iv}, or
5 or 6 membered heterocycloalkyl optionally substituted by C_{1-6}-alkyl, or
C_{1-6}-alkyl or aryl, each of which is optionally substituted by
halo,
—O(CO)—C_{1-6}-alkyl, or
—NH(CO)R^d, wherein R^d is C_{1-6}-alkyl optionally substituted by halo or nitro, or R^d is aryl or a 5 or 6 membered heteroaryl, each of which is optionally substituted by halo, nitro, C_{1-6}-alkyl or C_{1-6}-haloalkyl;

B is halo,
CN,
NR^iR^{ii},
C_{1-6}-alkyl optionally substituted by CN, halo or C_{1-6}-alkoxy,
C_{1-6}-alkoxy,
C_{1-6}-haloalkoxy,
C_{3-6}-cycloalkyl,
—C(O)O—C_{1-6}-alkyl,
—C(O) NR^iR^{ii},
—C(O)—C_{1-6}-alkyl,
—S(O)_2—C_{1-6}-alkyl,
—S(O)_2—NR^iR^{ii}, or
(CR^{iii}R^{iv})_n-phenyl, or (CR^{iii}R^{iv})_n-5 or 6 membered heteroaryl wherein the phenyl or 5 or 6 membered heteroaryl moiety is optionally substituted by one or more substituent(s) selected from the group consisting of halo, CN, NR^iR^{ii}, C_{1-6}-alkyl optionally substituted by CN or C_{1-6}-alkoxy, C_{1-6}-alkoxy, C_{1-6}-haloalkoxy, C_{3-6}-cycloalkyl, —C(O)O—C_{1-6}-alkyl, —C(O)—NR^iR^{ii}, —C(O)—C_{1-6}-alkyl, —S(O)_2—C_{1-6}-alkyl, and —S(O)_2—NR^iR^{ii};

R^i and R^{ii} are each independently H, C_{1-6}-alkyl, C_{1-6}-alkyl-NR^{iii}R^{iv}, —(CO)O—C_{1-6}-alkyl, —C(O)—NR^{iii}R^{iv}, —C(O)—C_{1-6}-alkyl, —S(O)_2—C_{1-6}-alkyl or —S(O)_2—NR^{iii}R^{iv};

R^{iii} and R^{iv} are each independently H or C_{1-6}-alkyl;

m is 1 to 6;

n is 0 to 4; and

A is either a group of the formula (a) or (b):

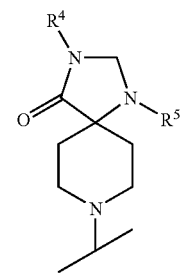
(a)

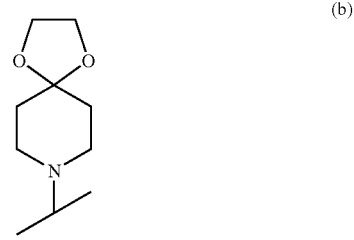
(b)

wherein

R⁴ is is H or C_{1-6}-alkyl; and

R⁵ is aryl optionally substituted by halo;

or a pharmaceutically acceptable salt thereof.

In detail, the present invention relates to compounds of the general formula (I):

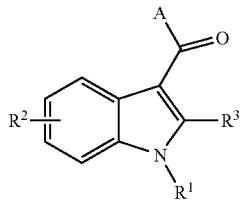

(I)

wherein $R^1$ is H,
$C_{1-6}$-alkyl,
aryl, 5 or 6 membered heteroaryl or sulfonylaryl each of which is optionally substituted by one or more B,
—$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6-membered heteroaryl, each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B, or $R^1$ and $R^3$ together with the indole ring to which they are attached form a 5 or 6 membered heterocycloalkyl which is optionally substituted by =O;

there is one or more $R^2$, wherein each $R^2$ is the same or different, $R^2$ is one or more H,
OH,
halo,
CN,
nitro, or
$C_{1-6}$-alkyl optionally substituted by —$NR^{iii}R^{iv}$, $C_{1-6}$-alkoxy, —O—$CH_2$—$C_{2-6}$-alkenyl, or benzyloxy, or two $R^2$ together with the indole ring to which they are attached form an oxo or dioxo bridge;

$R^3$ is H,
halo,
or —(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$,
5 or 6 membered heterocycloalkyl optionally substituted by $C_{1-6}$-alkyl, or
$C_{1-6}$-alkyl or aryl, each of which is optionally substituted by halo, —O(CO)—$C_{1-6}$-alkyl, or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O) $NR^iR^{ii}$,
—C(O)—$C_{1-6}$-alkyl,
—$S(O)_2$—$C_{1-6}$-alkyl,
—$S(O)_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ and $R^{iv}$ are each independently H or $C_{1-6}$-alkyl;

m is 1 to 6;

n is 0 to 4; and

A is either a group of the formula (a) or (b):

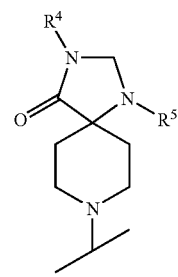

(a)

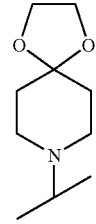

(b)

wherein $R^4$ is is H or $C_{1-6}$-alkyl;

$R^5$ is aryl optionally substituted by halo;

or a pharmaceutically acceptable salt thereof.

A further embodiment of the invention includes compounds of formula (I) as described herein, or pharmaceutically acceptable salts thereof, with the proviso that compounds with A of group (b) and $R^1=R^2=R^3=H$; and compounds with A of group (b) and $R^2=OH$, $C_{1-6}$-alkoxy, or benzyloxy at the 5-position of the indole are excluded.

A further embodiment of the invention includes compounds of formula (I) as described herein, or pharmaceutically acceptable salts thereof, with the proviso that compounds with A of group (b) and $R^1=R^2=R^3=H$; and compounds with A of group (b) and $R^2=OH$, $C_{1-6}$-alkoxy, —O—CH$_2$—C$_{2-6}$-alkenyl or benzyloxy at the 5-position of the indole are excluded.

A further embodiment of the invention includes compounds of formula (I) as described herein, or pharmaceutically acceptable salts thereof, with the proviso that $R^1=R^2=R^3=H$ is excluded.

Also encompassed by the compounds of formula (I) are the following compounds of formula (I-a) according to the invention:

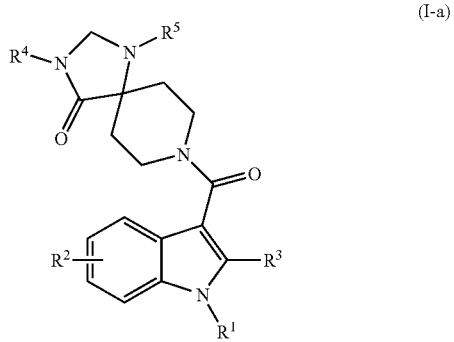

(I-a)

wherein $R^1$ to $R^5$ are as defined hereinabove for formula (I).

Preferred compounds of formula (I-a) are those compounds wherein, $R^1$ is H,

C$_{1-6}$-alkyl, aryl, 5 or 6 membered heteroaryl, sulfonylaryl, each of which is optionally substituted by one or more B, —(CH$_2$)$_m$—R$^a$ wherein R$^a$ is:

CN,

NR$^i$R$^{ii}$, or

C$_{3-6}$-cycloalkyl, 4 to 7 membered-heterocycloalkyl, aryl, or 5 or 6 membered heteroaryl each of which is optionally substituted by one or more B, or —(CH$_2$)$_n$—(CO)—R$^b$ or —(CH$_2$)$_n$—(SO$_2$)—R$^b$, wherein R$^b$ is:

C$_{1-6}$-alkoxy,

NR$^i$R$^{ii}$, or 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by =O;

there is one or more $R^2$, wherein each $R^2$ is the same or different, $R^2$ is one or more of H,

OH, halo,

C$_{1-6}$-alkyl optionally substituted by —NR$^{iii}$R$^{iv}$, or

C$_{1-6}$-alkoxy;

$R^3$ is H, or

—(CO)—R$^c$, wherein R$^c$ is:

—(CH$_2$)$_n$—NR$^i$R$^{ii}$,

—(CH$_2$)$_n$—NR$^{iii}$R$^{iv}$, 5 or 6 membered heterocycloalkyl optionally substituted by C$_{1-6}$-alkyl, or C$_{1-6}$-alkyl or aryl, each of which is optionally substituted by halo;

B is halo,

NH$_2$,

C$_{1-6}$-alkyl optionally substituted by CN or C$_{1-6}$-alkoxy,

C$_{1-6}$-alkoxy,

C$_{1-6}$-haloalkoxy,

C$_{3-6}$-cycloalkyl,

—C(O)O—C$_{1-6}$-alkyl, or

—(CR$^{iii}$R$^{iv}$)$_n$-phenyl, wherein the phenyl is optionally substituted by one or more substituent(s) selected from the group consisting of halo, C$_{1-6}$-alkyl optionally substituted by CN or halo, and C$_{1-6}$-alkoxy;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;

R$^{iii}$ and R$^{iv}$ are each independently H or C$_{1-6}$-alkyl;

m is 1 to 6;

n is 0 to 4;

$R^4$ is is H or C$_{1-6}$-alkyl; and $R^5$ is aryl optionally substituted by halo;

or a pharmaceutically acceptable salt thereof.

Most preferred compounds of formula (I-a) are those compounds wherein, $R^1$ is H, C$_{1-6}$-alkyl, phenyl, thiazolyl, pyridinyl, pyridazinyl, pyrimidinyl, oxazolyl, isoxazolyl, pyrazolyl, imidazolyl, or sulfonylphenyl, each of which is optionally substituted by one or more B, —(CH$_2$)$_m$—R$^a$ wherein R$^a$ is:

CN,

NR$^i$R$^{ii}$, or

C$_{3-6}$-cycloalkyl, oxetanyl, piperazinyl, tetrahydropyranyl, morpholinyl, phenyl, pyridinyl, pyrimidinyl, pyridazinyl, oxazolyl, isoxazolyl, pyrazolyl or imidazolyl, each of which is optionally substituted by one or more B, or —(CH$_2$)$_n$—(CO)—R$^b$ or —(CH$_2$)$_n$—(SO$_2$)—R$^b$, wherein R$^b$ is:

C$_{1-6}$-alkoxy,

NR$^i$R$^{ii}$, or oxetanyl, piperidinyl, piperazinyl, morpholinyl or phenyl, each of which is optionally substituted by one or more B, or $R^1$ and $R^3$ together with the indole ring to which they are attached form a 5 or 6 membered heterocycloalkyl which is optionally substituted by (CO);

there is one or more $R^2$, wherein each $R^2$ is the same or different, $R^2$ is one or more of H, OH, Cl, Br, or $C_{1-6}$-alkyl optionally substituted by —$NR^{iii}R^{iv}$, OMe or OEt;

$R^3$ is H, or
—(CO)—$R^c$, wherein $R^c$ is:
—$(CH_2)_n$—$NR^iR^{ii}$,
—$(CH_2)_n$—$NR^{iii}R^{iv}$,
oxetanyl, piperidinyl, piperazinyl, or morpholinyl, each of which is optionally substituted by $C_{1-6}$-alkyl, or
$C_{1-6}$-alkyl or aryl, each of which is optionally-substituted by Cl;

B is halo,
$NH_2$,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
or —$(CR^{iii}R^{iv})_n$-phenyl, wherein the phenyl is optionally substituted by one or more substituent(s) selected from the group consisting of halo, $C_{1-6}$-alkyl optionally substituted by CN or halo, and $C_{1-6}$-alkoxy;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ and $R^{iv}$ are each independently H or $C_{1-6}$-alkyl;

m is 1 to 6;

n is 0 to 4;

$R^4$ is is H or $C_{1-6}$-alkyl; and $R^5$ is aryl optionally substituted by halo;

or a pharmaceutically acceptable salt thereof.

Further preferred according to the invention are compounds of formula (I-a), wherein $R^1$ is H,
$C_{1-6}$-alkyl,
phenyl, optionally substituted by one or more B,
—$(CH_2)_m$—$R^a$ wherein $R^a$ is $NR^iR^{ii}$, or
—$(CH_2)_n$—(CO)—$R^b$, wherein $R^b$ is $NR^iR^{ii}$;

there is one or more $R^2$, wherein each $R^2$ is the same or different, $R^2$ is one or more of H, Cl, Br, or $C_{1-6}$-alkyl;

$R^3$ is H, or
—(CO)—$R^c$, wherein $R^c$ is:
—$(CH_2)_n$—$NR^iR^{ii}$,
—$(CH_2)_n$—$NR^{iii}R^{iv}$, or
$C_{1-6}$-alkyl, optionally substituted by Cl;

B is halo, $R^i$ and $R^{ii}$ are each independently H, $C_{1-6}$-alkyl, or $C_{1-6}$-alkyl-$NR^{iii}R^{iv}$;

$R^{iii}$ and $R^{iv}$ are each independently H or $C_{1-6}$-alkyl;

m is 1 to 6;

n is 0 to 4;

$R^4$ is is H or $C_{1-6}$-alkyl; and $R^5$ is aryl optionally substituted by halo;

or a pharmaceutically acceptable salt thereof.

Further preferred are compounds of formula (I-a) according to any one of the embodiments as described hereinabove, wherein $R^2$ is one or two halogen atom(s) and $R^1$, $R^3$, $R^4$ and $R^5$ are as described herein.

Further preferred are compounds of formula (I-a) according to any one of the embodiments as described hereinabove, wherein $R^2$ is a halogen atom at the 6-position of the indole. Preferably, the halogen atom at the 6-position of the indole is Cl.

Further preferred are compounds of formula (I-a) according to any one of the embodiments as described hereinabove, wherein one $R^2$ is $C_{1-6}$-alkyl or halogen atom at the 5-position of the indole, and one $R^2$ is a halogen atom at the 6-position of the indole. Preferably, $R^2$ at the 5-position of the indole is F or Me, and $R^2$ at the 6-position of the indole is Cl.

Further preferred are compounds of formula (I-a) according to any one of the embodiments as described hereinabove, wherein $R^3$ is $C_{1-6}$-alkyl.

Further preferred are compounds of formula (I-a) according to any one of the embodiments as described hereinabove, wherein $R^3$ is $C_{1-6}$-alkyl and $R^2$ is H.

Further preferred are compounds of formula (I-a) according to any one of the embodiments as described hereinabove, wherein either $R^3$ is $C_{1-6}$-alkyl and $R^2$ is H or $R^3$ is H and $R^2$ is a halogen, and in particular Cl, in the 6-position of the indole.

The following compounds are encompassed by present invention:

2-[6-Chloro-3-(3-methyl-4-oxo-1-phenyl-1,3,8-triaza-spiro[4.5]decane-8-carbonyl)-indol-1-yl]-N,N-dimethyl-acetamide;

8-[6-Chloro-1-(3,5-difluoro-benzyl)-1H-indole-3-carbonyl]-3-methyl-1-phenyl-1,3,8-triaza-spiro[4.5]decan-4-one;

2-[6-Chloro-3-(3-methyl-4-oxo-1-phenyl-1,3,8-triaza-spiro[4.5]decane-8-carbonyl)-indol-1-yl]-N-methyl-acetamide;

8-(1-Benzyl-6-chloro-1H-indole-3-carbonyl)-3-methyl-1-phenyl-1,3,8-triaza-spiro[4.5]decan-4-one;

8-[6-Chloro-1-(3-chloro-2-fluoro-benzyl)-1H-indole-3-carbonyl]-3-methyl-1-phenyl-1,3,8-triaza-spiro[4.5]decan-4-one;

8-[6-Chloro-1-(2-dimethylamino-ethyl)-1H-indole-3-carbonyl]-3-methyl-1-phenyl-1,3,8-triaza-spiro[4.5]decan-4-one;

2-[6-Chloro-3-(3-methyl-4-oxo-1-phenyl-1,3,8-triaza-spiro[4.5]decane-8-carbonyl)-indol-1-yl]-N-(2-dimethylamino-ethyl)-acetamide;

8-(1-Benzyl-2-methyl-1H-indole-3-carbonyl)-1-phenyl-1,3,8-triaza-spiro[4.5]decan-4-one;

8-[(1-benzyl-2-methyl-1H-indol-3-yl)carbonyl]-3-methyl-1-phenyl-1,3,8-triazaspiro[4.5]decan-4-one;

8-(6-Chloro-1H-indole-3-carbonyl)-1-phenyl-1,3,8-triaza-spiro[4.5]decan-4-one;

2-[6-Chloro-3-(3-methyl-4-oxo-1-phenyl-1,3,8-triaza-spiro[4.5]decane-8-carbonyl)-indol-1-yl]-acetamide;

8-(1-Benzyl-2-methyl-1H-indole-3-carbonyl)-1-(4-chlorophenyl)-1,3,8-triaza-spiro[4.5]decan-4-one;

8-(1H-Indole-3-carbonyl)-1-phenyl-1,3,8-triaza-spiro[4.5]decan-4-one; and

8-[(6-Chloro-1H-indol-3-yl)carbonyl]-3-methyl-1-phenyl-1,3,8-triazaspiro[4.5]decan-4-one.

Also encompassed by the compounds of formula (I) are the following compounds of formula (I-b) according to the invention:

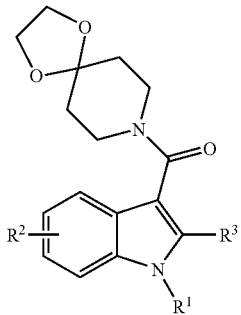

(I-b)

wherein $R^1$ to $R^3$ are as defined hereinabove for formula (I).

Preferred compounds of formula (I-b) are those compounds wherein, $R^1$ is H,
C$_{1-6}$-alkyl,
aryl, 5 or 6 membered heteroaryl, or sulfonylaryl, each of which is optionally substituted by one or more B,
—(CH$_2$)$_m$—R$^a$ wherein R$^a$ is:
CN,
NR$^i$R$^{ii}$, or
C$_{3-6}$-cycloalkyl, 4 to 7 membered-heterocycloalkyl, aryl, or 5 or 6 membered heteroaryl, each of which is optionally substituted by one or more B,
or —(CH$_2$)$_n$—(CO)—R$^b$ or —(CH$_2$)$_n$—(SO$_2$)—R$^b$, wherein R$^b$ is:
C$_{1-6}$-alkoxy,
NR$^i$R$^{ii}$, or
4 to 7 membered-heterocycloalkyl, aryl, each of which is optionally substituted by one or more B, or $R^1$ and $R^3$ together with the indole ring to which they are attached form a 5 or 6 membered heterocycloalkyl which is optionally substituted by =O;

there is one or more $R^2$, wherein each $R^2$ is the same or different, $R^2$ is one or more H, halo, or C$_{1-6}$-alkyl optionally substituted by —NR$^{iii}$R$^{iv}$;

$R^3$ is H, or
—(CO)—R$^c$, wherein R$^c$ is:
—(CH$_2$)$_n$—NR$^i$R$^{ii}$,
—(CH$_2$)$_n$—NR$^{iii}$R$^{iv}$,
5 or 6 membered heterocycloalkyl optionally substituted by C$_{1-6}$-alkyl, or
C$_{1-6}$-alkyl or aryl, each of which is optionally substituted by halo, B is halo,
NH$_2$,
C$_{1-6}$-alkyl optionally substituted by CN or C$_{1-6}$-alkoxy,
C$_{1-6}$-alkoxy,
C$_{1-6}$-haloalkoxy,
C$_{3-6}$-cycloalkyl,
—C(O)O—C$_{1-6}$-alkyl,
or —(CR$^{iii}$R$^{iv}$)$_n$-phenyl, wherein the phenyl is optionally substituted by one or more substituent(s) selected from the group consisting of halo, C$_{1-6}$-alkyl optionally substituted by CN or halo, and C$_{1-6}$-alkoxy;

$R^i$ and $R^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;

$R^{iii}$ and $R^{iv}$ are each independently H or C$_{1-6}$-alkyl;

m is 1 to 6; and n is 0 to 4;

or a pharmaceutically acceptable salt thereof.

Most preferred compounds of formula (I-b) are those compounds wherein, $R^1$ is H,
C$_{1-6}$-alkyl,
phenyl, thiazolyl, pyridinyl, pyridazinyl, pyrimidinyl, oxazolyl, isoxazolyl, pyrazolyl, imidazolyl, or sulfonylphenyl, each of which is optionally substituted by one or more B,
—(CH$_2$)$_m$—R$^a$ wherein R$^a$ is:
CN,
NR$^i$R$^{ii}$, or
C$_{3-6}$-cycloalkyl, oxetanyl, piperazinyl, tetrahydropyranyl, morpholinyl, phenyl, pyridinyl, pyrimidinyl, pyridazinyl, oxazolyl, isoxazolyl, pyrazolyl or imidazolyl, each of which is optionally substituted by one or more B,
or —(CH$_2$)$_n$—(CO)—R$^b$ or —(CH$_2$)$_n$—(SO$_2$)—R$^b$, wherein R$^b$ is:
C$_{1-6}$-alkoxy,
NR$^i$R$^{ii}$, or
oxetanyl, piperidinyl, piperazinyl, morpholinyl or phenyl, each of which is optionally substituted by one or more B, or $R^1$ and $R^3$ together with the indole ring to which they are attached form a 5 or 6 membered heterocycloalkyl which is optionally substituted by =O;

there is one or more $R^2$, wherein each $R^2$ is the same or different, $R^2$ is one or more H, Cl, Br, or C$_{1-6}$-alkyl optionally substituted by —NR$^{iii}$R$^{iv}$;

$R^3$ is H, or
—(CO)—R$^c$, wherein R$^c$ is:
—(CH$_2$)$_n$—NR$^i$R$^{ii}$,
—(CH$_2$)$_n$—NR$^{iii}$R$^{iv}$,
oxetanyl, piperidinyl, piperazinyl, or morpholinyl, each of which is optionally substituted by C$_{1-6}$-alkyl, or
C$_{1-6}$-alkyl or aryl, each of which is optionally substituted by Cl;

B is halo,
NH$_2$,
C$_{1-6}$-alkyl optionally substituted by CN or C$_{1-6}$-alkoxy,
C$_{1-6}$-alkoxy,
C$_{1-6}$-haloalkoxy,
C$_{3-6}$-cycloalkyl,
—C(O)O—C$_{1-6}$-alkyl, or
—(CR$^{iii}$R$^{iv}$)$_n$-phenyl, wherein the phenyl is optionally substituted by one or more substituent(s) selected from the group consisting of halo, C$_{1-6}$-alkyl optionally substituted by CN or halo, and C$_{1-6}$-alkoxy;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;

$R^{iii}$ and $R^{iv}$ are each independently H or $C_{1-6}$-alkyl;

m is 1 to 6; and n is 0 to 4;

or a pharmaceutically acceptable salt thereof.

Further preferred are compounds of formula (I-b) according to any one of the embodiments as described hereinabove, wherein $R^2$ is one or two halogen atom(s).

Further preferred are compounds of formula (I-b) according to any one of the embodiments as described hereinabove, wherein $R^2$ is a halogen atom at the 6-position of the indole. Preferably, the halogen atom at the 6-position of the indole is Cl.

Further preferred are compounds of formula (I-b) according to any one of the embodiments as described hereinabove, wherein one $R^2$ is $C_{1-6}$alkyl or halogen atom at the 5-position of the indole, and one $R^2$ is a halogen atom at the 6-position of the indole. Preferably, $R^2$ at the 5-position of the indole is F or Me, and $R^2$ at the 6-position of the indole is Cl.

Further preferred are compounds of formula (I-b) according to any one of the embodiments as described hereinabove, wherein $R^3$ is $C_{1-6}$-alkyl.

Further preferred are compounds of formula (I-b) according to any one of the embodiments as described hereinabove, wherein $R^3$ is $C_{1-6}$-alkyl and $R^2$ is H.

Further preferred are compounds of formula (I-b) according to any one of the embodiments as described hereinabove, wherein either $R^3$ is $C_{1-6}$-alkyl and $R^2$ is H or $R^3$ is H and $R^2$ is a halogen, and in particular Cl, in the 6-position of the indole.

The invention encompasses for example the following compounds: (1-Benzyl-2-methyl-1H-indol-3-yl)-(1,4-dioxa-8-aza-spiro[4.5]dec-8-yl)-methanone; and 8-[(6-chloro-1H-indol-3-yl)carbonyl]-1,4-dioxa-8-azaspiro[4.5]decane.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprise administering a therapeutically effective amount of a compound of formula (i), (I-a), or (I-b) or a pharmaceutically acceptable salt thereof.

The invention also encompasses pharmaceutical compositions comprising a compound of formula (I), (I-a) or (I-b) which pharmaceutical compositions are useful for the treatment of dysmenorrhea, hypertension, chronic heart failure, inappropriate secretion of vasopressin, liver cirrhosis, nephrotic syndrome, obsessive compulsive disorder, anxiety and depressive disorders.

The invention also encompasses processes for the preparation of compounds of formula (I), (I-a) or (I-b).

In a certain embodiment, the compounds of formula (I) of the invention can be prepared according to a process comprising reacting a compound of formula (II):

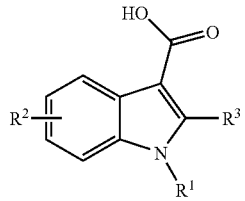

with a compound of formula A-H, to obtain a compound of formula (I), wherein $R^1$, $R^2$, $R^3$ and A are as defined hereinabove for formula (I). The synthesis is optionally performed in an inert solvent.

Amide couplings as such are known to the person skilled in the art. Optionally, the carboxylic acid II is activated, either in a first step or in situ during amide synthesis. Activated species of carboxylic acid II are for example acid chlorides, anhydrides or mixed anhydrides, azides, or activated esters. Examples for activated esters are pentachloro- or pentafluorophenole esters of carboxylic acid II. Activation reagents for activation of the carboxylic acid during amide synthesis are for example carbodiimides which form activated esters as intermediates, namely the respective O-acyl-ureas. Examples for carbodiimides are N,N'-dicyclohexylcarbodiimide (DCC), 1-ethyl-3-(3-dimethylaminopropyl) carbodiimide hydrochloride (EDC) or N,N'-diisopropylcarbodiimide (DIC), each of which can optionally be combined with coupling reagents such as N-hydroxybenzotriazole (HOBt), O-(7-azabenzotriazole-1-yl)-N,N,N'N'-tetramethyluronium hexafluorophosphate (HATU), 4-dimethylaminopyridine (DMAP) and the like. A further reagent for activation is N,N'-carbonyl-di-imidazole, forming the respective acid imidazolide as an activated intermediate.

This process is described more in details in general scheme and procedure A hereinafter.

In another embodiment, the compounds of formula (I) of the invention can be prepared according to a process comprising reacting a compound of formula (I-1):

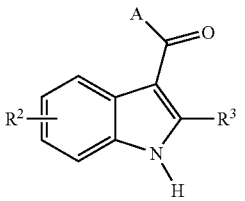

with a compound of formula $R^1$—X, to obtain a compound of formula (I), wherein X is halo, preferably Cl, $R^1$ and $R^4$ are as defined hereinabove for formula-(I) but are different from H and $R^2$ and $R^3$ are as defined hereinabove for formula (I). This process is described more in details in general scheme and procedure B hereinafter.

In still another embodiment, the compounds of formula (I-a) of the invention can be prepared according to a process comprising reacting a compound of formula (I-a1):

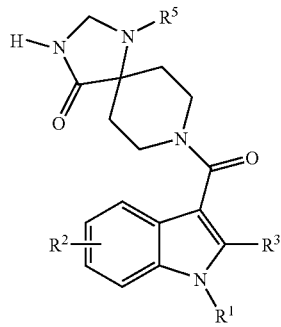

(I-a1)

with a compound of formula R⁴—X, to obtain a compound of formula (I-a), wherein X is halo, preferably Cl, $R^1$, $R^4$ and $R^5$ are as defined hereinabove for formula (I) but are different from H and $R^2$ and $R^3$ are as defined hereinabove for formula (I). This process is described more in details in general scheme and procedure C hereinafter.

As already mentioned hereinabove, the aforementioned processes are described more in details with the following general schemes and procedures A to C. General scheme and procedure D show how to prepare useful inter-mediates of formula (II).

General Scheme A

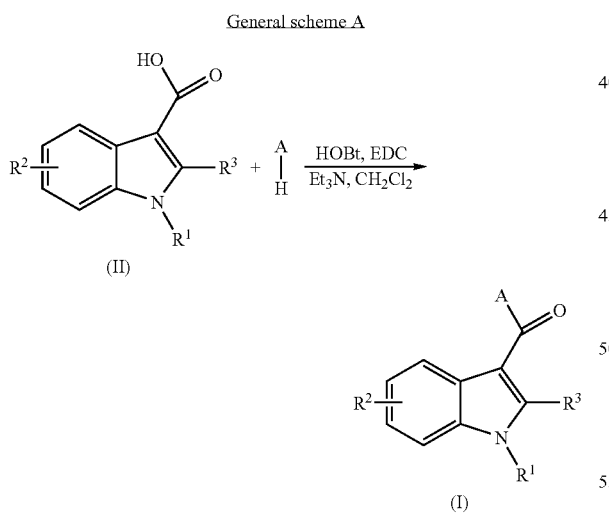

Compounds of formula (I) can be prepared via an amide coupling between an indole 3-carboxylic acid (II) and a piperidine (A-H). Indole 3-carboxylic acids (II) are either commercially available or readily prepared using a procedure described in. *J. Med. Chem.* 1991, 34, 140, or prepared following the general scheme D. The piperidine derivatives A-H are either commercially available or prepared using published procedures.

General Scheme B

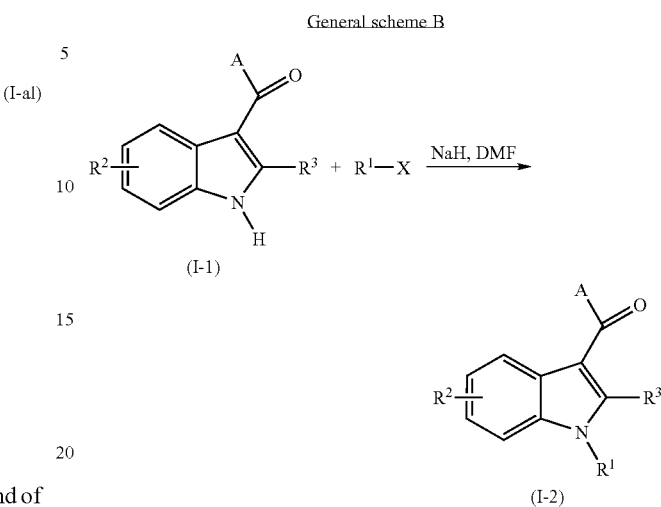

Compounds of formula (I-2) (compounds of formula (I) wherein $R^1$ and $R^4$ are both different from H), can be prepared by alkylation of the indole derivative of formula (I-1), (compounds of formula (I) wherein $R^1$ is H and $R^4$ is different from H), with an electrophile of formula $R^1$—X (commercially available, wherein X is halo, preferably Cl or Br) using standard procedures. Derivatives (I-1) are prepared using the method described in the general scheme A.

General Scheme C

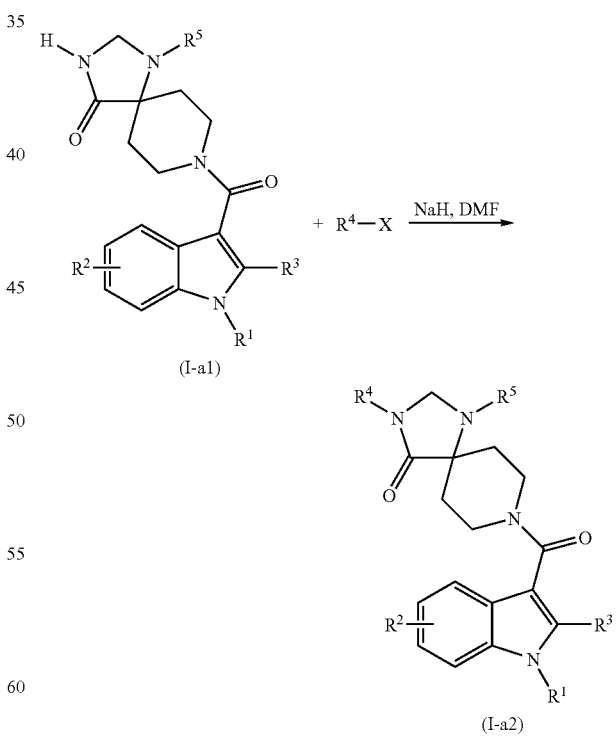

Compounds of formula (I-a2) (compounds of formula (I-a) wherein $R^1$ and $R^4$ both different from H), can be prepared by an alkylation of a derivative (I-a1) (compounds of formula (I-a), wherein $R^4$ is H and $R^1$ is different from H) with an electrophile of formula R⁴—X (commercially available, wherein X is halo, preferably Cl or Br) using standard procedures. Derivatives of formula (I-a1) are prepared using the method described in the general scheme A General Scheme D

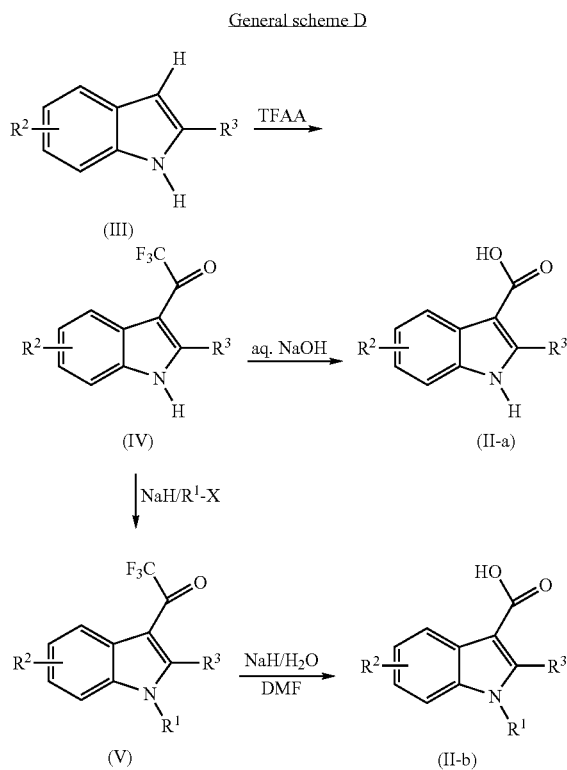

The treatment of an indole derivative of formula (III) with the trifluoroacetic anhydride in DMF afforded the intermediate of formula (IV) which can be then hydrolysed with an aqueous sodium hydroxide solution to give the 3-carboxylic acid-indole derivative of formula (II-a). Alternatively, the compound of formula (IV) could react with an electrophile of formula R¹—X (commercially available, wherein X is halo, preferably Cl or Br and R¹ is other than H) to give the compound of formula (V), which is then converted to the corresponding carboxylic acid derivative of formula (II-b) with NaH/H$_2$O in DMF (see *J. Org Chem.*, 1993, 10, 2862).

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds of formula (I) of the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method, and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture is then added to each well of a 96 well plate, followed by 50 ul of 4 nM 3H-Vasopressin (American Radiolabeled Chemicals). For total binding measurement 100 ul of binding buffer are added to the respective wells, for non-specific binding 100 ul of 8.4 mM cold vasopressin and for compound testing 100 ul of a serial dilution of each compound in 2% DMSO. The plate is incubated 1 h at room temperature, centrifuged 1 min at 1000 g and counted on a Packard Top-Count. Non-specific binding counts are subtracted from each well, and data is normalized to the maximum specific binding set at 100%. To calculate an IC 50 the curve is fitted using a non-linear regression model (XLfit), and the Ki is calculated using the Cheng-Prussoff equation.

| Compound of Example | Ki (nM) |
| --- | --- |
| 1 | 368 |
| 2 | 367 |
| 7 | 156 |
| 8 | 37 |
| 9 | 21 |
| 10 | 14 |
| 11 | 45 |
| 13 | 73 |
| 14 | 184 |
| 15 | 424 |
| 16 | 284 |

The present invention also provides pharmaceutical compositions containing compounds of formula (I), (I-a) or (I-b) or their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants.

They can also contain still other therapeutically valuable substances.

The invention also provides a method for preparing compositions of the invention which comprises bringing one or more compounds of formula I, I-a, or I-b and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The compounds of the invention can be administered orally, for example, in the form of tablets, coated tablets, dragées, hard and soft-gelatin capsules, solutions, emulsions, or suspensions. The compounds of the invention can be administered rectally, for example, in the form of suppositories or parenterally, for example, in the form of injectable solutions.

Compounds of formula (I) have good activity on the V1a receptor. Therefore, the invention provides methods for the treatment of dysmenorrhea, hypertension, chronic heart failure, inappropriate secretion of vasopressin, liver cirrhosis, nephrotic syndrome, obsessive compulsive disorder, anxiety and depressive disorders. Such methods comprise administering a therapeutically effective amount of a compound of formula (I) or a pharmaceutically acceptable salt thereof. The preferred indications with regard to the present invention are the treatment of anxiety and depressive disorders.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I), (I-a) or (I-b) should be appropriate, although the above upper limit can also be exceeded when necessary.

The following Examples illustrate the present invention without limiting it. All temperatures are given in degrees Celsius.

Example A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool; the suppositories are then removed from the moulds and packed individually in wax paper or metal foil.

EXAMPLES

Where journal references are cited in the examples, the example was performed using the starting material listed with the reactants and conditions cited in the reference. All procedures in such references are well known to those of ordinary skill in the art. All journal references cited herein are incorporated by reference.

General Procedure I—Amide Coupling:

To a stirred solution of an indole-3-carboxylic acid derivative of type (II) (1 mmol) in 10 ml $CH_2Cl_2$ was added (1.3 mmol) EDC, (1.3 mmol) HOBt, (1.3 mmol) $Et_3N$ and (1 mmol) of the amine derivative (A-H). The mixture was stirred overnight at room temperature and then poured onto water and extracted with $CH_2Cl_2$. The combined organic phases were dried over $Na_2SO_4$ and concentrated in vacuo. Flash chromatography or preparative HPLC afforded a compound of formula (I).

General Procedure II—Alkylation:

To a stirred solution of a derivative of general formula (I-1) in DMF was added 2.1 eq. NaH (60% in oil). The mixture was stirred at room temperature for 30 min. and then the electrophilic reactant $R^1$—X (1.1 eq.) was added. The mixture was stirred an additional 14 hours at 60° C. and then poured onto water and extracted with ethyl acetate. The combined organic phases were dried over $Na_2SO_4$ and concentrated in vacuo. Purification by preparative HPLC afforded the corresponding derivatives of general formula (I-2).

Acid Intermediates of Formula II

Acid 1

1-Benzyl-2-methyl-1H-indole-3-carboxylic acid

To a stirred solution of 0.50 g (3.10 mmol) 2-methyl-1H-indole-3-carboxylic acid (described in *J. Heterocyclic Chem.* 1977, 14, 1123) in 5 ml DMF were added 0.27 g (6.75 mmol) of NaH (60% in oil). The mixture was stirred at room temperature for 30 min. and then 0.39 ml (3.28 mmol) of benzyl bromid were added. The mixture was stirred for one additional hour and then poured onto water and extracted with ethyl acetate. The combined organic phases were dried over $Na_2SO_4$ and concentrated in vacuo. Crystallization from $Et_2O$ afforded 1-benzyl-2-methyl-1H-indole-3-carboxylic acid.

Acid 2

6-Chloro-1H-indole-3-carboxylic acid a) 1-(6-Chloro-1H-indol-3-yl)-2,2,2-trifluoro-ethanone To a solution of 15.0 g (98.9 mmol) 6-chloroindole in 150 ml dry N,N-dimethylformamide were added dropwise under argon 15.8 ml (114 mmol) trifluoroacetic anhydride at 0° C. After stirring at 0° C. for 2 h another portion of 15.8 ml (114 mmol) trifluoroacetic anhydride was added, and stirring was continued for 30 min. Quenching with saturated aqueous sodium carbonate solution was followed by extraction with three portions of ethyl acetate. The combined organic layers were dried over sodium sulfate and concentrated in vacuo. The residue was triturated in tert.-butyl methyl ether. Filtration gave 20.4 g (82%) of the title compound as a white solid. The mother liquor was concentrated in vacuo and triturated in tert.-butyl methyl ether to give another portion of 1.2 g (5%) of the title compound.

MS m/e (%): 246 (M−H$^+$, 100)

b) 6-Chloro-1H-indole-3-carboxylic acid

A solution of 21.6 g (87.2 mmol) 1-(6-chloro-1H-indol-3-yl)-2,2,2-trifluoro-ethanone in 110 ml of a 4 M aqueous solution of potassium hydroxide was heated at reflux for 2 h. After cooling to 0° C. neutralisation with 36.7 ml of a concentrated aqueous hydrochloric acid solution a white solid precipitated from the solution. The solid was collected by filtration and washed with water. Drying in high vacuo at 80° C. gave 16.4 g (96%) of the title compound as a light yellow solid.

MS m/e (%): 194 (M−H$^+$, 100)

Examples of Compounds of Formula (I-a)

Example 1

8-[(1-Benzyl-2-methyl-1H-indol-3-yl)carbonyl]-3-methyl-1-phenyl-1,3,8-triazaspiro[4.5]decan-4-one Amide coupling according to general procedure I:
Amine: 3-Methyl-1-phenyl-1,3,8-triaza-spiro[4.5]decan-4-one (described in *App. Radiat. Isot.* 1995, 46, 911;
Acid: 1-Benzyl-2-methyl-1H-indole-3-carboxylic acid;

ES-MS m/e (%): 493.5 (M+H$^+$).

Example 2

8-(1-Benzyl-2-methyl-1H-indole-3-carbonyl)-1-phenyl-1,3,8-triaza-spiro[4.5]decan-4-one Amide coupling according to general procedure I:
Amine: 1-Phenyl-1,3,8-triaza-spiro[4.5]decan-4-one (commercially-available);
Acid: 1-Benzyl-2-methyl-1H-indole-3-carboxylic acid;
ES-MS m/e (%): 479.4 (M+H$^+$).

Example 3

8-(1-Benzyl-2-methyl-1H-indole-3-carbonyl)-1-(4-chloro-phenyl)-1,3,8-triaza-spiro[4.5]decan-4-one Amide coupling according to general procedure I:
Amine: 1-(4-Chloro-phenyl)-1,3,8-triaza-spiro[4.5]decan-4-one (described in WO2005040166A1);
Acid: 1-Benzyl-2-methyl-1H-indole-3-carboxylic acid;
ES-MS m/e (%): 513.1 (M+H$^+$).

Example 4

8-(6-Chloro-1H-indole-3-carbonyl)-1-phenyl-1,3,8-triaza-spiro[4.5]decan-4-one

Amide coupling according to general procedure I:
Amine: 1-Phenyl-1,3,8-triaza-spiro[4.5]decan-4-one (commercially available);
Acid: 6-Chloro-1H-indole-3-carboxylic acid;
ES-MS m/e (%): 409 (M+H$^+$).

Example 5

8-(1H-Indole-3-carbonyl)-1-phenyl-1,3,8-triaza-spiro[4.5]decan-4-one

Amide coupling according to general procedure I:
Amine: 1-Phenyl-1,3,8-triaza-spiro[4.5]decan-4-one (commercially available);
Acid: 1H-Indole-3-carboxylic acid (commercially available);
ES-MS m/e (%): 375.3 (M+H$^+$).

Example 6

8-[(6-Chloro-1H-indol-3-yl)carbonyl]-3-methyl-1-phenyl-1,3,8-triazaspiro[4.5]decan-4-one Following the general procedure I, the coupling of 3-methyl-1-phenyl-1,3,8-triaza-spiro[4.5]decan-4-one (described in *App. Radiat. Isot.* 1995, 46, 911) with 6-chloro-1H-indole-3-carboxylic acid gave the title compound.

ES-MS m/e (%): 423.5 (M+H$^+$).

Example 7

8-({6-Chloro-1-[2-(dimethylamino)ethyl]-1H-indol-3-yl}carbonyl)-3-methyl-1-phenyl-1,3,8-triazaspiro[4.5]decan-4-one Following the general procedure II, the coupling of 8-[(6-chloro-1H-indol-3-yl)carbonyl]-3-methyl-1-phenyl-1,3,8-triazaspiro[4.5]decan-4-one with (commercially available) (2-chloro-ethyl)-dimethyl-amine gave the title compound.

ES-MS m/e (%): 494.2 (M+H$^+$).

Example 8

2-{6-Chloro-3-[(3-methyl-4-oxo-1-phenyl-1,3,8-triazaspiro[4.5]dec-8-yl)carbonyl]-1H-indol-1-yl}-N-methylacetamide Following the general procedure II, the coupling of 8-[(6-chloro-1H-indol-3-yl)carbonyl]-3-methyl-1-phenyl-1,3,8-triazaspiro[4.5]decan-4-one with (commercially available) 2-chloro-N-methyl-acetamide gave the title compound.

ES-MS m/e (%): 494.2 (M+H$^+$).

Example 9

8-{[6-Chloro-1-(3,5-difluorobenzyl)-1H-indol-3-yl]carbonyl}-3-methyl-1-phenyl-1,3,8-triazaspiro[4.5]decan-4-one Following the general procedure II, the coupling of 8-[(6-chloro-1H-indol-3-yl)carbonyl]-3-methyl-1-phenyl-1,3,8-triazaspiro[4.5]decan-4-one with (commercially available) 1-chloromethyl-3,5-difluoro-benzene gave the title compound.

ES-MS m/e (%): 549.2 (M+H$^+$).

Example 10

2-{6-Chloro-3-[(3-methyl-4-oxo-1-phenyl-1,3,8-triazaspiro[4.5]dec-8-yl)carbonyl]-1H-indol-1-yl}-N,N-dimethylacetamide Following the general procedure II, the coupling of 8-[(6-chloro-1H-indol-3-yl)carbonyl]-3-methyl-1-phenyl-1,3,8-triazaspiro[4.5]decan-4-one with (commercially available) 2-chloro-N,N-dimethyl-acetamide gave the title compound.

ES-MS m/e (%): 508.2 (M+H$^+$).

Example 11

8-[(1-Benzyl-6-chloro-1H-indol-3-yl)carbonyl]-3-methyl-1-phenyl-1,3,8-triazaspiro[4.5]decan-4-one Following the general procedure II, the coupling of 8-[(6-chloro-1H-indol-3-yl)carbonyl]-3-methyl-1-phenyl-1,3,8-triazaspiro[4.5]decan-4-one with (commercially available) benzyl chloride gave the title compound.

ES-MS m/e (%): 513.2 (M+H$^+$).

Example 12

2-{6-Chloro-3-[(3-methyl-4-oxo-1-phenyl-1,3,8-triazaspiro[4.5]dec-8-yl)carbonyl]-1H-indol-1-yl}acetamide Following the general procedure II, the coupling of 8-[(6-chloro-1H-indol-3-yl)carbonyl]-3-methyl-1-phenyl-1,3,8-triazaspiro[4.5]decan-4-one with (commercially available) 2-chloro-acetamide gave the title compound.

ES-MS m/e (%): 480.2 (M+H$^+$).

Example 13

8-{[6-Chloro-1-(3-chloro-2-fluorobenzyl)-1H-indol-3-yl]carbonyl}-3-methyl-1-phenyl-1,3,8-triazaspiro[4.5]decan-4-one Following the general procedure, the coupling of 8-[(6-chloro-1H-indol-3-yl)carbonyl]-3-methyl-1-phenyl-1,3,8-triazaspiro[4.5]decan-4-one with (commercially-available) 1-chloro-3-chloromethyl-2-fluoro-benzene gave the title compound.

ES-MS m/e (%): 565.2 (M+H$^+$).

Example 14

2-{6-Chloro-3-[(3-methyl-4-oxo-1-phenyl-1,3,8-triazaspiro[4.5]dec-8-yl)carbonyl]-1H-indol-1-yl}-N-[2-(dimethylamino)ethyl]acetamide a) [6-Chloro-3-(3-methyl-4-oxo-1-phenyl-1,3,8-triaza-spiro[4.5]decane-8-carbonyl)-indol-1-yl]-acetic acid Following the general procedure II, the coupling of 8-[(6-chloro-1H-indol-3-yl)carbonyl]-3-methyl-1-phenyl-1,3,8-triazaspiro[4.5]decan-4-one with (commercially available) bromo-acetic acid gave the title compound.

ES-MS m/e (%): 479.1 (M−H$^+$).

b) 2-{6-Chloro-3-[(3-methyl-4-oxo-1-phenyl-1,3,8-triaza-spiro[4.5]dec-8-yl)carbonyl]-1H-indol-1-yl}-N-[2-(dimethylamino)ethyl]acetamide A solution of [6-chloro-3-(3-methyl-4-oxo-1-phenyl-1,3,8-triaza-spiro[4.5]decane-8-carbonyl)-indol-1-yl]-acetic acid in DMF was treated sequentially with 1 eq. of O-(7-azabenzotriazol-1-yl)-N,N,N',N'-tetramethyluronium hexafluorophosphate, 1 eq. of N,N-diisopropylethylamine and 1 eq. of N,N-dimethylethylenediamine. The mixture was shaken at room temperature for 12 h, concentrated and purified by prep. HPLC to give the title compound.

ES-MS m/e (%): 551.2 (M+H$^+$).

Examples of Compounds of Formula (I-b)

Example 15

(1-Benzyl-2-methyl-1H-indol-3-yl)-(1,4-dioxa-8-aza-spiro[4.5]dec-8-yl)-methanone Amide coupling according to general procedure I:
Amine: 1,4-Dioxa-8-aza-spiro[4.5]decane (commercially available);
Acid: 1-Benzyl-2-methyl-1H-indole-3-carboxylic acid;

ES-MS m/e (%): 391.5 (M+H$^+$).

Example 16

8-[(6-Chloro-1H-indol-3-yl)carbonyl]-1,4-dioxa-8-azaspiro[4.5]decane

Amide coupling according to general procedure I:
Amine: 1,4-Dioxa-8-aza-spiro[4.5]decane (commercially available);
Acide: 6-chloro-1H-indole-3-carboxylic acid.

The invention claimed is:
1. A compound of formula (I):

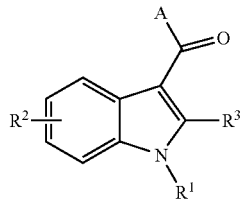

(I)

wherein
R¹ is H,
C$_{1-6}$-alkyl,
aryl, 5 or 6 membered heteroaryl or sulfonylaryl, each of which is optionally substituted by one or more B,
—(CH$_2$)$_m$—R$^a$ wherein R$^a$ is:
CN,
OR$^i$,
NR$^i$R$^{ii}$, or
C$_{3-6}$-cycloalkyl, 4 to 7 membered-heterocycloalkyl, aryl, or 5 or 6 membered heteroaryl, each of which is optionally substituted by one or more B,
or —(CH$_2$)$_n$—(CO)—R$^b$ or —(CH$_2$)$_n$—(SO$_2$)—R$^b$, wherein R$^b$ is:
C$_{1-6}$-alkyl,
C$_{1-6}$-alkoxy,
C$_{3-6}$-cycloalkyl,
—(CH$_2$)$_m$—NR$^{iii}$R$^{iv}$,
NR$^i$R$^{ii}$, or
C$_{3-6}$-cycloalkyl, 4 to 7 membered-heterocycloalkyl, aryl, or 5 or 6 membered heteroaryl, each of which is optionally substituted by one or more B,
or R¹ and R³ together with the indole ring to which they are attached form a 5 or 6 membered heterocycloalkyl which is optionally substituted by =O;
there is one or more R², wherein each R² is the same or different,
R² is one or more H,
OH,
halo,
CN,
nitro,
C$_{1-6}$-alkyl optionally substituted by —NR$^{iii}$R$^{iv}$,
C$_{1-6}$-alkoxy,
—O—CH$_2$—C$_{2-6}$-alkenyl, or
benzyloxy,
or two R² together with the indole ring to which they are attached form an oxo or dioxo bridge;
R³ is H,
halo, or
—(CO)—R$^c$, wherein R$^c$ is:
C$_{1-6}$-alkyl,
—(CH$_2$)$_n$—NR$^i$R$^{ii}$,
—(CH$_2$)$_n$—NR$^{iii}$R$^{iv}$, or
5 or 6 membered heterocycloalkyl optionally substituted by C$_{1-6}$-alkyl, or
C$_{1-6}$-alkyl or aryl, each of which is optionally substituted by halo, —O(CO)—C$_{1-6}$-alkyl, or —NH(CO)R$^d$, wherein R$^d$ is C$_{1-6}$-alkyl optionally substituted by halo or nitro,
or R$^d$ is aryl or a 5 or 6 membered heteroaryl, each of which is optionally substituted by halo, nitro, C$_{1-6}$-alkyl or C$_{1-6}$-haloalkyl;

B is halo,
CN,
NR$^i$R$^{ii}$,
C$_{1-6}$-alkyl optionally substituted by CN, halo or C$_{1-6}$-alkoxy,
C$_{1-6}$-alkoxy,
C$_{1-6}$-haloalkoxy,
C$_{3-6}$-cycloalkyl,
—C(O)O—C$_{1-6}$-alkyl,
—C(O)NR$^i$R$^{ii}$,
—C(O)—C$_{1-6}$-alkyl,
—S(O)$_2$—C$_{1-6}$-alkyl,
—S(O)$_2$—NR$^i$R$^{ii}$, or
(CR$^{iii}$R$^{iv}$)$_n$-phenyl or (CR$^{iii}$R$^{iv}$)$_n$-5 or 6 membered heteroaryl, wherein the phenyl or 5 or 6 membered heteroaryl moiety is optionally substituted by one or more substituent(s) selected from the group consisting of halo, CN, NR$^i$R$^{ii}$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)—NR$^i$R$^{ii}$, —C(O)—C$_{1-6}$-alkyl, —S(O)$_2$—C$_{1-6}$-alkyl, and —S(O)$_2$—NR$^i$R$^{ii}$;
R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;
R$^{iii}$ and R$^{iv}$ are each independently H or C$_{1-6}$-alkyl;
m is 1 to 6;
n is 0 to 4; and
A is either a group of the formula (a) or (b):

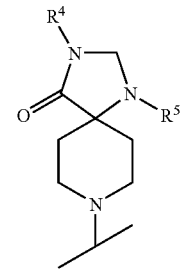

(a)

wherein
R⁴ is H or C$_{1-6}$-alkyl; and
R⁵ is aryl optionally substituted by halo;
or a pharmaceutically acceptable salt thereof.
2. The compound of claim 1, wherein
R¹ is H,
C$_{1-6}$-alkyl,
aryl, 5 or 6 membered heteroaryl or sulfonylaryl each of which is optionally substituted by one or more B,
—(CH$_2$)$_m$—R$^a$ wherein R$^a$ is:
CN,
OR$^i$,
NR$^i$R$^{ii}$, or
C$_{3-6}$-cycloalkyl, 4 to 7 membered-heterocycloalkyl, aryl, or 5 or 6 membered heteroaryl, each of which is optionally substituted by one or more B,
or —(CH$_2$)$_n$—(CO)—R$^b$ or —(CH$_2$)$_n$—(SO$_2$)—R$^b$, wherein R$^b$ is:
C$_{1-6}$-alkyl,
C$_{1-6}$-alkoxy, $C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B,
or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more H,
OH,
halo,
CN,
nitro, or
$C_{1-6}$-alkyl optionally substituted by —$NR^{iii}R^{iv}$, $C_{1-6}$-alkoxy, —O—$CH_2$—$C_{2-6}$-alkenyl, or benzyloxy,
or two $R^2$ together with the indole ring to which they are attached form an oxo or dioxo bridge;
$R^3$ is H,
halo, or
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl, or
$C_{1-6}$-alkyl or aryl, each of which is optionally substituted by halo, —O(CO)— $C_{1-6}$-alkyl, or —NH(CO)$R^d$, wherein $R^d$ is $C_{1-6}$-alkyl optionally substituted by halo or nitro,
or $R^d$ is aryl or a 5 or 6 membered heteroaryl, each of which is optionally substituted by halo, nitro, $C_{1-6}$-alkyl or $C_{1-6}$-haloalkyl;
B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O)$NR^iR^{ii}$,
—C(O)—$C_{1-6}$-alkyl,
—$S(O)_2$—$C_{1-6}$-alkyl,
—$S(O)_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of halo, CN, $NR^iR^{ii}$, $C_{1-6}$-alkyl substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;
$R^{iii}$ and $R^{iv}$ are each independently H or $C_{1-6}$-alkyl;
m is 1 to 6;
n is 0 to 4; and A is either a group of the formula (a) or (b):

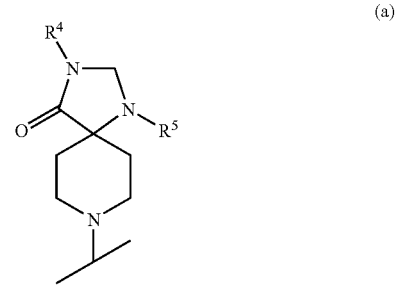

(a)

wherein
$R^4$ is H or $C_{1-6}$-alkyl; and
$R^5$ is aryl optionally substituted by halo;
or a pharmaceutically acceptable salt thereof.

3. The compound of claim 1 having formula (I-a),

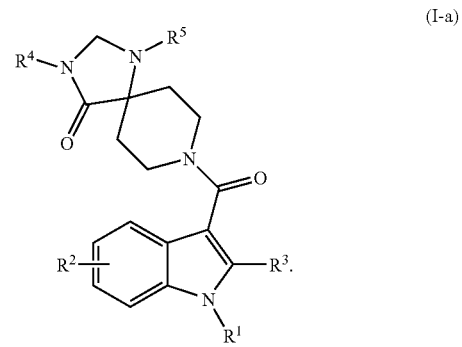

(I-a)

4. The compound of claim 3, wherein
$R^1$ is H,
$C_{1-6}$-alkyl,
aryl, 5 or 6 membered heteroaryl, sulfonylaryl, each of which is optionally substituted by one or more B,
—$(CH_2)_m$—$R^a$ wherein $R^a$ is:
CN,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkoxy,
$NR^iR^{ii}$, or
4 to 7 membered-heterocycloalkyl, aryl, or 5 or 6 membered heteroaryl each of which is optionally substituted by one or more B,
or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more of H,
OH,
halo,
$C_{1-6}$-alkyl optionally substituted by —$NR^{iii}R^{iv}$, or
$C_{1-6}$-alkoxy;

$R^3$ is H, or
—(CO)—$R^c$, wherein $R^c$ is:
—$(CH_2)_n$—$NR^iR^{ii}$,
—$(CH_2)_n$—$NR^{iii}R^{iv}$,
5 or 6 membered heterocycloalkyl optionally substituted by $C_{1-6}$-alkyl, or
$C_{1-6}$-alkyl or aryl, each of which is optionally substituted by halo;
B is halo,
$NH_2$,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl, or
—$(CR^{iii}R^{iv})_n$-phenyl, wherein the phenyl is optionally substituted by one or more substituent(s) selected from the group consisting of halo, $C_{1-6}$-alkyl optionally substituted by CN or halo and $C_{1-6}$-alkoxy;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;
$R^{iii}$ and $R^{iv}$ are each independently H or $C_{1-6}$-alkyl;
m is 1 to 6;
n is 0 to 4;
$R^4$ is H or $C_{1-6}$-alkyl; and
$R^5$ is aryl optionally substituted by halo;
or a pharmaceutically acceptable salt thereof.

5. The compound of formula (I-a) according to claim 3, wherein
$R^1$ is H,
$C_{1-6}$-alkyl,
phenyl, thiazolyl, pyridinyl, pyridazinyl, pyrimidinyl, oxazolyl, isoxazolyl, pyrazolyl, imidazolyl, or sulfonylphenyl, each of which is optionally substituted by one or more B,
—$(CH_2)_m$—$R^a$ wherein $R^a$ is:
CN,
$NR^iR^{ii}$, or
$C_{3-6}$-cycloalkyl, oxetanyl, piperazinyl, tetrahydropyranyl, morpholinyl, phenyl, pyridinyl, pyrimidinyl, pyridazinyl, oxazolyl, isoxazolyl, pyrazolyl or imidazolyl, each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkoxy,
$NR^iR^{ii}$, or
oxetanyl, piperidinyl, piperazinyl, morpholinyl or phenyl, each of which is optionally substituted by one or more B,
or $R^1$ and $R^3$ together with the indole ring to which they are attached form a 5 or 6 membered heterocycloalkyl which is optionally substituted by (CO);
there is one or more $R^2$, wherein each $R^2$ is the same or different,
$R^2$ is one or more of H, OH, Cl, Br, or $C_{1-6}$-alkyl optionally substituted by —$NR^{iii}R^{iv}$, OMe or OEt;
$R^3$ is H, or
—(CO)—$R^c$, wherein $R^c$ is:
—$(CH_2)_n$—$NR^iR^{ii}$,
—$(CH_2)_n$—$NR^{iii}R^{iv}$,
oxetanyl, piperidinyl, piperazinyl, or morpholinyl, each of which is optionally substituted by $C_{1-6}$-alkyl, or
$C_{1-6}$-alkyl or aryl, each of which is optionally substituted by Cl;
B is halo,
$NH_2$,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
or —$(CR^{iii}R^{iv})_n$-phenyl, wherein the phenyl is optionally substituted by one or more substituent(s) selected from the group consisting of halo, $C_{1-6}$-alkyl optionally substituted by CN or halo, and $C_{1-6}$-alkoxy;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;
$R^{iii}$ and $R^{iv}$ are each independently H or $C_{1-6}$-alkyl;
m is 1 to 6;
n is 0 to 4;
$R^4$ is H or $C_{1-6}$-alkyl; and
$R^5$ is aryl optionally substituted by halo;
or a pharmaceutically acceptable salt thereof.

6. The compound of claim 3, wherein
$R^1$ is H,
$C_{1-6}$-alkyl,
phenyl, optionally substituted by one or more B,
—$(CH_2)_m$—$R^a$ wherein $R^a$ is $NR^iR^{ii}$, or
—$(CH_2)_n$—(CO)—$R^b$, wherein $R^b$ is $NR^iR^{ii}$;
there is one or more $R^2$, wherein each $R^2$ is the same or different,
$R^2$ is one or more of H, Cl, Br, or $C_{1-6}$-alkyl;
$R^3$ is H, or
—(CO)—$R^c$, wherein $R^c$ is:
—$(CH_2)_n$—$NR^iR^{ii}$,
—$(CH_2)_n$—$NR^{iii}R^{iv}$, or
$C_{1-6}$-alkyl, optionally substituted by Cl;
B is halo,
$R^i$ and $R^{ii}$ are each independently H, $C_{1-6}$-alkyl, or $C_{1-6}$-alkyl-$NR^{iii}R^{iv}$;
$R^{iii}$ and $R^{iv}$ are each independently H or $C_{1-6}$-alkyl;
m is 1 to 6;
n is 0 to 4;
$R^4$ is H or $C_{1-6}$-alkyl; and
$R^5$ is aryl optionally substituted by halo;
or a pharmaceutically acceptable salt thereof.

7. The compound of claim 3, wherein $R^2$ is one or two halogen atom(s).

8. The compound of claim 7, wherein $R^2$ is a halogen atom at the 6-position of the indole.

9. The compound of claim 5, wherein $R^2$ is Cl at the 6-position of the indole.

10. The compound of 3, wherein one $R^2$ is $C_{1-6}$-alkyl or halogen atom at the 5-position of the indole, and one $R^2$ is a halogen atom at the 6-position of the indole.

11. The compound of claim 10, wherein the $R^2$ at the 5-position of the indole is F or Me and the $R^2$ at the 6-position of the indole is Cl.

12. The compound of claim 3, wherein $R^3$ is $C_{1-6}$alkyl.

13. The compound of claim 12, wherein $R^2$ is hydrogen.

14. The compound of claim 3, wherein $R^3$ is $C_{1-6}$alkyl and $R^2$ is H or wherein $R^3$ is hydrogen and $R^2$ is halogen.

15. The compound of claim 14, wherein $R^2$ is Cl at the 6-position of the indole.

16. The compound of claim 1, selected from the group consisting of:
- 2-[6-Chloro-3-(3-methyl-4-oxo-1-phenyl-1,3,8-triaza-spiro[4.5]decane-8-carbonyl)-indol-1-yl]-N,N-dimethyl-acetamide;
- 8-[6-Chloro-1-(3,5-difluoro-benzyl)-1H-indole-3-carbonyl]-3-methyl-1-phenyl-1,3,8-triaza-spiro[4.5]decan-4-one;
- 2-[6-Chloro-3-(3-methyl-4-oxo-1-phenyl-1,3,8-triaza-spiro[4.5]decane-8-carbonyl)-indol-1-yl]-N-methyl-acetamide;
- 8-(1-Benzyl-6-chloro-1H-indole-3-carbonyl)-3-methyl-1-phenyl-1,3,8-triaza-spiro[4.5]decan-4-one;
- 8-[6-Chloro-1-(3-chloro-2-fluoro-benzyl)-1H-indole-3-carbonyl]-3-methyl-1-phenyl-1,3,8-triaza-spiro[4.5]decan-4-one;
- 8-[6-Chloro-1-(2-dimethylamino-ethyl)-1H-indole-3-carbonyl]-3-methyl-1-phenyl-1,3,8-triaza-spiro[4.5]decan-4-one; and
- 2-[6-Chloro-3-(3-methyl-4-oxo-1-phenyl-1,3,8-triaza-spiro[4.5]decane-8-carbonyl)-indol-1-yl]-N-(2-dimethylamino-ethyl)-acetamide.

17. The compound of claim 1, selected from the group consisting of
- 8-(1-Benzyl-2-methyl-1H-indole-3-carbonyl)-1-phenyl-1,3,8-triaza-spiro[4.5]decan-4-one;
- 8-[(1-benzyl-2-methyl-1H-indol-3-yl)carbonyl]-3-methyl-1-phenyl-1,3,8-triazaspiro[4.5]decan-4-one;
- 8-(6-Chloro-1H-indole-3-carbonyl)-1-phenyl-1,3,8-triaza-spiro[4.5]decan-4-one;
- 2-[6-Chloro-3-(3-methyl-4-oxo-1-phenyl-1,3,8-triaza-spiro[4.5]decane-8-carbonyl)-indol-1-yl]-acetamide
- 8-(1-Benzyl-2-methyl-1H-indole-3-carbonyl)-1-(4-chloro-phenyl)-1,3,8-triaza-spiro[4.5]decan-4-one;
- 8-(1H-Indole-3-carbonyl)-1-phenyl-1,3,8-triaza-spiro[4.5]decan-4-one; and
- 8-[(6-Chloro-1H-indol-3-yl)carbonyl]-3-methyl-1-phenyl-1,3,8-triazaspiro[4.5]decan-4-one.

18. A pharmaceutical composition comprising a compound of formula I

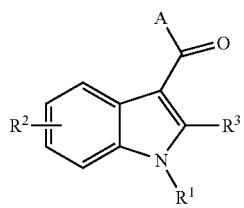
(I)

wherein
$R^1$ is H,
$C_{1-6}$-alkyl,
aryl, 5 or 6 membered heteroaryl or sulfonylaryl, each of which is optionally substituted by one or more B,
—$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B,
or —$(CH_2)_n$—(CO)—$R^b$ or —$(CH_2)_n$—$(SO_2)$—$R^b$,
wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B,
or $R^1$ and $R^3$ together with the indole ring to which they are attached form a 5 or 6 membered heterocycloalkyl which is optionally substituted by =O;
there is one or more $R^2$, wherein each $R^2$ is the same or different,
$R^2$ is one or more H,
OH,
halo,
CN,
nitro,
$C_{1-6}$-alkyl optionally substituted by —$NR^{iii}R^{iv}$,
$C_{1-6}$-alkoxy,
—O—$CH_2$—$C_{2-6}$-alkenyl, or
benzyloxy,
or two $R^2$ together with the indole ring to which they are attached form an oxo or dioxo bridge;
$R^3$ is H,
halo, or
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$,
5 or 6 membered heterocycloalkyl optionally substituted by $C_{1-6}$-alkyl, or
$C_{1-6}$-alkyl or aryl, each of which is optionally substituted by halo, —O(CO)— $C_{1-6}$-alkyl, or —NH(CO)$R^d$, wherein $R^d$ is $C_{1-6}$-alkyl optionally substituted by halo or nitro,
or $R^d$ is aryl or a 5 or 6 membered heteroaryl, each of which is optionally substituted by halo, nitro, $C_{1-6}$-alkyl or $C_{1-6}$-haloalkyl;
B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O) $NR^iR^{ii}$,
—C(O)—$C_{1-6}$-alkyl,
—$S(O)_2$—$C_{1-6}$-alkyl,
—$S(O)_2$—$NR^iR^{ii}$, or
$(CR^{iii}R^{iv})_n$-phenyl or $(CR^{iii}R^{iv})_n$-5 or 6 membered heteroaryl, wherein the phenyl or 5 or 6 membered heteroaryl moiety is optionally substituted by one or more substituent(s) selected from the group consisting of halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —$S(O)_2$—$C_{1-6}$-alkyl, and —$S(O)_2$—$NR^iR^{ii}$;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;

$R^{iii}$ and $R^{iv}$ are each independently H or $C_{1-6}$-alkyl;
m is 1 to 6;
n is 0 to 4; and
A is either a group of the formula (a) or (b):
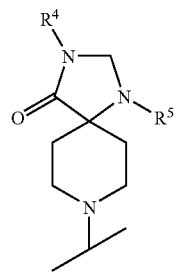 (a)
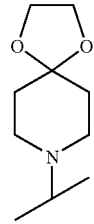 (b)
wherein
$R^4$ is H or $C_{1-6}$-alkyl; and
$R^5$ is aryl optionally substituted by halo;
or a pharmaceutically acceptable salt thereof and a pharmaceutically acceptable carrier.
19. The composition of claim 18, wherein the compound of formula I has formula I-a.
* * * * *